United States Patent [19]

Kraska et al.

[11] 4,357,332

[45] Nov. 2, 1982

[54] SUBSTITUTED PIPERAZINES HAVING IMMUNE REGULANT ACTIVITY

[75] Inventors: Allen R. Kraska, East Lyme; Joseph G. Lombardino, Niantic, both of Conn.

[73] Assignee: Pfizer Inc., New York, N.Y.

[21] Appl. No.: 146,846

[22] Filed: May 5, 1980

[51] Int. Cl.$^3$ .................. A61K 31/495; C07D 295/08
[52] U.S. Cl. .................................. 424/250; 544/401; 544/394
[58] Field of Search .......................... 544/401; 424/250

[56] References Cited

U.S. PATENT DOCUMENTS

| | | | |
|---|---|---|---|
| 3,051,709 | 8/1962 | Shapiro et al. | 544/401 |
| 3,668,206 | 6/1972 | Narayanan et al. | 544/401 |
| 3,935,267 | 1/1976 | Hauck et al. | 544/401 |
| 3,968,218 | 7/1976 | Bouillon et al. | 544/401 |
| 4,069,221 | 1/1978 | Yonsa | 544/401 |
| 4,255,426 | 3/1981 | Kraska | 544/401 |

FOREIGN PATENT DOCUMENTS 5012  5/1967  France .

OTHER PUBLICATIONS

Chem. Abs. 89 59771 (1978).

*Primary Examiner*—Anton H. Sutto
*Attorney, Agent, or Firm*—Charles J. Knuth; Peter C. Richardson; Allen Bloom

[57] ABSTRACT

1-Benzyl- and 1-phenyl-4-(2-hydroxy-3-benzyloxypropyl)-piperazines useful as immune regulants are disclosed. Also disclosed are pharmaceutical compositions containing the novel compounds and a method of regulating immune response of a warm blooded animal by administration of the novel compounds.

7 Claims, No Drawings

SUBSTITUTED PIPERAZINES HAVING IMMUNE REGULANT ACTIVITY

BACKGROUND OF THE INVENTION

This invention relates to novel 1-benzyl and 1-phenyl-4-(2-hydroxy-3-benzyloxypropyl)-piperazines useful as immune regulants.

A number of compounds have been known in the art to be useful as anti-inflammatory agents, for example, the corticosteroids, phenylbutazone, indomethacin and various 3,4-dihydro-4-oxo-2H-1,2-benzothiazine-4-carboxamide-1,1-dioxides, such as those disclosed in U.S. Pat. No. 3,591,584. Accordingly, these compounds have been of therapeutic value in the treatment of arthritic and other inflammatory conditions such as rheumatoid arthritis. Such conditions have also been treated by administration of immuno-regulatory agents, such as levamisole, as described for example, in Arthritis Rheumatism, 20, 1445 (1977) and Lancet, 1, 393 (1976).

It is also known that biological vaccines such as *Corynebacterium pavrum* and BCG, a viable strain of *Mycobacterium bovis*, have utility as immune stimulants of the reticulo-endothelial system and are thereby capable of increasing the resistance of a warm blooded animal to tumors. However, the use of these agents has been restricted by hepatic-renal toxicity, granuloma formation, neutropenia and inconsistent therapeutic effects. Accordingly, it has been of continuing interest to develop non-biological, systemically active immune stimulants for use in increasing the resistance of a host to tumors. For discussions of the stimulation of cell-mediated immunity and antitumoral activity, see Herberman, Adv. Cancer Res., 19, 207 (1971), Jordan and Merigan, Ann. Rev. Pharmacol. 15, 157 (1975), Levy and Wheelock, Adv. Cancer Res., 20, 131 (1972) and Sinkovics, Post Graduate Medicine, 59, 110 (1976).

SUMMARY OF THE INVENTION

The present invention relates to novel 1-benzyl- and 1-phenyl-4-(2-hydroxy-3-benzyloxypropyl)-piperazines having immune regulant activity. More specifically, the compounds of the present invention are those of the formula:

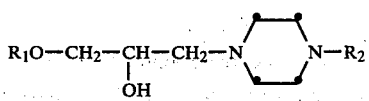

and the pharmaceutically acceptable acid addition salts thereof, wherein $R_1$ is benzyl or monosubstituted benzyl; and $R_2$ is phenyl, monosubstituted phenyl, benzyl or monosubstituted benzyl; said substituents being selected from alkyl of 1 to 3 carbon atoms, alkoxy of 1 to 3 carbon atoms, chloro, bromo and fluoro.

Preferably $R_2$ is benzyl or monosubstituted benzyl and most preferably, benzyl. $R_1$ is preferably benzyl. A particularly preferred compound is 1-benzyl-4-(2-hydroxy-3-benzyloxypropyl)piperazine.

The present invention also includes pharmaceutical compositions containing the novel compounds of formula I together with a pharmaceutically acceptable carrier or diluent. Preferred pharmaceutical compositions are those containing the preferred novel compounds of formula I as set forth hereinabove.

Also embraced by the present invention is a method of immune regulation in a warm blooded animal which comprises administering to the animal an effective immune regulant amount of a compound of formula I, preferably selected from the preferred compounds of formula I described hereinabove.

DETAILED DESCRIPTION OF THE INVENTION

The novel compounds of formula I are readily prepared by the reaction of an appropriate 2,3-epoxypropylbenzyl ether with a suitable substituted piperazine. The 2,3-epoxypropylbenzyl ether is prepared by reaction of an appropriately substituted benzyl alcohol with an allyl halide, preferably allyl chloride or bromide. The reaction is generally conducted in the presence of an alkali metal hydride, such as sodium hydride, in an inert organic solvent, such as dimethylformamide, at temperatures from about 50° C. to 120° C., preferably about 75° C. to 100° C. The allyl-benzyl ether formed in this reaction is then oxidized to the corresponding 2,3-epoxypropyl-benzyl ether by conventional oxidative methods using, for example, a peroxy acid such as perbenzoic acid, m-chloroperbenzoic acid and the like. The reaction is generally conducted in an inert organic solvent, such as methylene chloride, chloroform and the like, at a temperature from about 10° C. to 50° C., preferably at about room temperature.

The 2,3-epoxypropyl-benzyl ether is reacted with an appropriate 1-$R_2$-substituted-piperazine. The reaction is generally effected by heating the reactants at a temperature from about 75° C. to about 250° C., preferably from about 150° C. to 200° C., preferably employing a small excess of the $R_2$-substituted-piperazine. The time necessary for completion of the reaction will vary with the temperature employed, but is generally from about 15 minutes to about 2 hours at the preferred temperatures in the range from 150° C. to 200° C. The reaction is preferably conducted without the addition of a solvent, but if desired, a reaction inert solvent, such as dimethylformamide and the like, may be employed.

The pharmaceutically acceptable acid addition salts of the novel substituted piperazines of formula I are readily prepared by contacting the free base with the appropriate mineral or organic acid in either aqueous solution or in a suitable organic solvent, for example, a lower alkanol having from 1 to 6 carbon atoms. The solid salt may then be obtained by precipitation or by evaporation of the solvent. The pharmaceutically acceptable acid addition salts of this invention include, but are not limited to, the hydrochloride, hydrobromide, hydroiodide, sulfate, bisulfate, nitrate, phosphate, acetate, lactate, maleate, fumarate, citrate, tartrate, succinate, gluconate, methane sulfonate, and the like.

The novel compounds of this invention and their pharmaceutically acceptable acid addition salts are useful as regulants of the immune response in warm blooded animals. These compounds are therefore useful in the treatment of conditions such as rheumatoid arthritis and other diseases associated with immune deficiency and accompanied by inflammation. Like the known compound levamisole, a compound employed for the treatment of rheumatoid arthritis, the compounds of the present invention act to regulate the immune response of the subject and thereby alleviate the underlying immune disorder by maintaining immune competence. In addition, the activity of the present novel compounds as immune regulants makes them useful in maintaining the immune response of a warm blooded animal to increase the resistance of the animal to tumors, the compound acting to stimulate the natural immune system of the subject to reject tumors.

The present invention therefore also embraces a method of immune regulation in a warm blooded animal by administering to the animal an effective immune regulant amount of a compound of formula I or a pharmaceutically acceptable acid addition salt thereof. In accord with this method, the compound of the present invention may be administered to the subject in need of treatment by conventional routes, such as orally or parenterally, at dosages in the amount of about 0.1 to about 75 mg/kg body weight of the subject per day, preferably about 0.15 to about 15 mg/kg. body weight per day. If desired, the immune competence of the subject being treated may be monitored following administration of the drug using conventional techniques well known in the art and the response of the subject to the drug determined.

The compounds of this invention may be used in pharmaceutical preparations containing the compound or a pharmaceutically acceptable acid addition salt thereof in combination with a pharmaceutically acceptable carrier or diluent. Suitable pharmaceutically acceptable carriers include inert solid fillers or diluents and sterile aqueous or organic solutions. The active compound will be present in such pharmaceutical compositions in an amount sufficient to provide the desired dosage amount in the range described above. Thus, for oral administration the compound may be combined with a suitable solid or liquid carrier or diluent to form capsules, tablets, powders, syrups, solutions, suspensions and the like. The pharmaceutical composition may, if desired, contain additional components such as flavorants, sweeteners, excipients and the like. For parenteral administration the compounds may be combined with sterile aqueous or organic media to form injectable solutions or suspensions. For example, solutions of the compounds of formula I in sesame or peanut oil, aqueous propylene glycol and the like may be used, as well as aqueous solutions or water soluble pharmaceutically acceptable acid addition salts of the compounds. The injectable solutions prepared in this manner may then be administered intravenously, interperitoneally, subcutaneously or intramuscularly, with intravenous and interperitoneal administration being preferred.

The immune regulant activity of the compounds of the present invention may be determined by such standard pharmacological tests as the stimulation in vitro of lymphocyte proliferation of murine thymus cells cultured in the presence of Concanavalin A (Con A) employing the general evaluation procedure of Merluzzi et al., see *Journal of Clinical and Experimental Immunology*, Vol. 22, p. 486 (1975). In this study, three different levels of peak lymphocyte stimulation assay (LSA) activity were established for the compounds undergoing evaluation, viz. those equal to Con A alone; those superior to Con A activity but less than levamisole, the standard compound of choice in this area; and those having an activity equal to levamisole. Compounds are considered to be active for the present purposes if they are superior to Concanavalin A.

The immune regulant activity of the compounds of the present invention may also be determined by an assessment of tumor rejection in, for example, the Sarcoma 180 J model. In this test, the increased life span (% ILS) is determined for a group of female CD-1 mice. The mice receive $10^6$ S—180 J cells, which are five to eight days old, by intraperitoneal administration. On the day following tumor inoculation the mice receive 0.1 ml. of the test compound formulated in Tween-glycerol at the desired dose level and are then observed until death or for forty days, whichever occurs first. The increased life span is then determined from the ratio of the mean survival time of drug treated mice to the mean survival time of untreated control group mice.

A further test for this purpose is the CaD2 adenocarcinoma model. In this model, a group of B6D2F1 female mice are implanted subcutaneously in the side with 1 $mm^2$ fragments of $CaD_2$ mammary adenocarcinoma. After 15 days, the primary tumor is surgically removed. The test compound is then administered orally at the desired dose level and the animals are monitored until death or for 100 days, whichever occurs first. The increased life span is then determined from the ratio of the mean survivial time of drug treated mice to the means survival time of untreated controlled group mice.

The present invention is illustrated by the following examples. However, it should be understood that the invention is not limited to the specific details of these examples.

EXAMPLE 1

Allylbenzyl ether

Sodium hydride (4.8 g, 0.2 mol, 50% dispersion in mineral oil) was added under nitrogen at room temperature to benzyl alcohol (21.6 g., 0.2 mol) in 150 ml. of dry dimethylformamide. The suspension was stirred at room temperature for 30 minutes and then heated at 60° C. for 30 minutes. Allyl bromide (24.2 g., 0.2 mol) was added to the suspension dropwise at 50° C. with stirring. The reaction mixture was heated at 90° C. for five and a half hours under nitrogen, cooled and stirred at room temperature overnight. The dimethylformamide was removed on a rotary evaporator and the resulting oil was extracted with ether, dried over sodium sulfate and the ether evaporated off. The resulting oil was purified on a silica gel column using hexane (500 ml) to remove the mineral oil, followed by methylene chloride (750 ml) to elute the desired product. Evaporation of the solvent yielded the title compound as a pale yellow liquid, 16 g., 54% yield.

EXAMPLE 2

2,3-Epoxypropyl-benzyl Ether

Allylbenzyl ether (1.50 g., 0.01 mol.), was dissolved in 36 ml. methylene chloride and treated with m-chloroperbenzoic acid (4.10 g, 0.02 mole) at room temperature for 17 hours. The mixture was then filtered and 100 ml of 5% sodium sulfite solution was added to the filtrate, followed by addition of 50 ml saturated sodium bicarbonate. The methylene chloride layer was separated, washed three times with sodium bicarbonate and once with water and dried over sodium sulfate. Removal of the methylene chloride under vacuum yielded the title compound as a pale gold oil, 1.44 g., 87% yield.

EXAMPLE 3

1-Benzyl-4-(2-hydroxy-3-benzyloxypropyl)piperazine Dihydrochloride 2,3-Epoxypropyl-benzyl ether (1.22 g., 0.0074 mole) and 1-benzylpiperazine (1.31 g, 0.0074 mole) were combined and heated under nitrogen at 150° C. for two and a half hours. The reaction mixture was diluted to 400 ml. with diethyl ether and anhydrous hydrogen chloride gas was bubbled through the solution while the solution was stirred and cooled. The solids formed were filtered, washed with diethyl ether and dried over phosphorus pentoxide under vacuum. The resulting solids were dissolved in 75 ml refluxing isopropanol, the solution filtered, evaporated down to a volume of 30 ml and allowed to cool slowly. The resulting crystals were broken up, filtered, washed with cold isopropanol and vacuum dried over phosphorus pentoxide to give the title compound, 2.18 g., 71% yield, m.p. 215°–216.5° C.

Analytical: Calcd. for $C_{21}H_{28}N_2O_2 \cdot 2HCl$: C, 61.02; H, 7.31; N, 6.78. Found: C, 60.48; H, 7.20; N, 6.75.

EXAMPLE 4

1-Phenyl-4-(2-hydroxy-3-benzyloxypropyl)-piperazine dihydrochloride

Following the procedure of Example 3, 2,3-epoxypropyl-benzyl ether and 1-phenylpiperazine are reacted to form the title compound.

EXAMPLE 5

Sarcoma 180J Model for Assessment of Tumor Rejection

Six female CD-1 mice (20–25 g) per group were treated intraperitoneally with $10^6$ S-180J cells, which were 5 to 8 days old. On the day following tumor inoculation the mice received 0.1 ml of the test compound formulated in the fat emulsion vehicle Intralipid (Cutter Laboratories). The drug was formulated by dissolving it in a minimum amount of alcohol and adding this solution to the Intralipid at the desired dose. The animals were then observed until death or 40 days, whichever occurred first. Results are expressed as percent increased life span (%ILS), defined as follows:

$$\% ILS = \frac{(S - S_C)}{S_C} \times 100$$

Where S=Mean Survival time of Drug Treated Mice;

and Sc=Mean Survival time of Mice in Control Group.

In a test of 1-benzyl-4-(2-hydroxy-3-benzyloxypropyl)-piperazine as described above at a dose of 15 mg/kg an ILS of 32% was obtained.

EXAMPLE 6

The immune regulant activity of 1-benzyl-4-(2-hydroxy-3-benzyloxypropyl)-piperazine was evaluated by determining its ability to stimulate, in vitro, the lymphocyte proliferation of murine thymus cells cultured in the presence of Concanavalin A (Con A) by employing the procedure of V. J. Merluzzi et al., essentially as described in the *Journal of Clinical and Experimental Immunology*, Vol. 22, p. 486 (1975). The cells were derived from male C57B1/6 mice of from 6–8 weeks of age, purchased from the Jackson Laboratories of Bar Harbor, Maine and Con A was obtained from Sigma Chemicals of St. Louis, Mo. Each cell culture (consisting of 0.10 ml. thymus cells stock solution, 0.05 ml. of Con A stock solution and 0.05 ml. of drug solution) was performed in quadruplicate and cellular proliferation was measured, after 48 hours of incubation at 37° C., by pulsing each culture with $^3$H-thymidine (0.01 ml. of specific activity 1.9 C/mM, obtained from Schwarz-Mann, Inc. of Orangeburg, N.Y.) and then determining the incorporation of $^3$H-thymidine into cellular desoxyribonucleic acid (DNA) by an assessment of radioactivity using a liquid scintillation counter. The results obtained in this manner are expressed quantitatively in terms of the average counts per minute (cpm) of $^3$H-thymidine incorporated at each drug level. On this basis, three different levels of peak activity were established in the present lymphocyte stimulation assay (LSA), defined as follows: a level equal to Con A alone (6,000±300 cpm) was assigned a negative value or score of zero; a level superior (10,000±700 cpm) to Con A activity but less than levamisole was scored as +; a level equal to levamisole (30,000±900 cpm) was scored as ++. The minimum effective concentration (MEC) was determined at an activity level with a score of +. Results obtained with the test compound 1-benzyl-4-(2-hydroxy-3-benzyloxypropyl)piperazine (Example 3) and corresponding results for levamisole were as follows:

| Example | Peak Activity | |
|---|---|---|
| | Activity Level | Drug Concentration (μg./ml.) |
| 3 | ++ | 0.04 |
| Levamisole | ++ | 28 |

| Potency at a + Level of Activity | |
|---|---|
| Example | MEC (μg./ml.) |
| 3 | 0.004 |
| Levamisole | 1.0 |

EXAMPLE 7

CaD2 Adenocarcinoma Model For Assessment of Antitumor Activity

B6D2F1 female mice were implanted subcutaneously in the side with 1 mm.$^2$ fragments of CaD2 mammary adenocarcinoma. The tumor was allowed to grow and after 15 days surgery was performed to remove the primary tumor. The test compound was administered orally, and the animals were monitored until death or 100 days, whichever occurred first. The mean survival time was determined for control group and drug treated animals and the % ILS, defined as in Example 5, determined. The results obtained for 1-benzyl-4-(2-hydroxy-3-benzyloxypropyl)-piperazine were as follows:

| Dose (mg./kg.) | % ILS |
|---|---|
| 2.5 | 81 |
| 10 | 39 |
| 40 | 32 |

We claim:
1. A compound of the formula

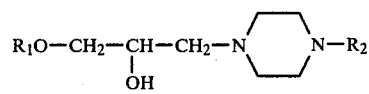

and the pharmaceutically acceptable addition salts thereof,
wherein $R_1$ and $R_2$ are each benzyl or monosubstituted benzyl, said substituent being selected from alkyl of 1 to 3 carbon atoms, alkoxy of 1 to 3 carbon atoms, chloro, bromo and fluoro.

2. A method of regulating cell-mediated immunity in a warm blooded animal comprising administering to said animal an immune-regulant effective amount of a compound of claim 1.

3. A method of claim 2 wherein $R_1$ and $R_2$ are each benzyl.

4. A compound of claim 1 wherein $R_2$ is benzyl.

5. A compound of claim 4 wherein $R_1$ is benzyl.

6. A pharmaceutical composition useful for regulating cell-mediated immunity comprising an immune-regulant effective amount of a compound of claim 1 and a pharmaceutically acceptable carrier.

7. A pharmaceutical composition of claim 6 wherein $R_1$ and $R_2$ are each benzyl.

* * * * *